United States Patent [19]  [11] Patent Number: 4,874,875
Navarrini et al.  [45] Date of Patent: Oct. 17, 1989

[54] PERFLUORO-AMINO-OXAZIRIDINES

[75] Inventors: Walter Navarrini, Milan, Italy; Darryl D. Desmarteu, Clemson, S.C.

[73] Assignee: Ausimont S.r.l., Milan, Italy

[21] Appl. No.: 268,248

[22] Filed: Nov. 7, 1988

[30] Foreign Application Priority Data

Nov. 10, 1987 [IT] Italy ................... 22576 A/87

[51] Int. Cl.$^4$ ........................... C07D 301/03
[52] U.S. Cl. ................................. 548/959
[58] Field of Search ......................... 548/959

[56] References Cited

U.S. PATENT DOCUMENTS 2,784,182  3/1957  Krimm et al. ............... 548/959
4,287,128  9/1981  Ratcliffe .................... 549/523

Primary Examiner—Mukund J. Shah
Assistant Examiner—Carol Lynn Cseh
Attorney, Agent, or Firm—Stevens, Davis, Miller & Mosher

[57] ABSTRACT

Perfluoro-oxaziridines, characterized by the presence of an aminic group in position 3 of the oxaziridine ring, of the formula:

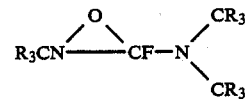

wherein each R is independently either F or a perfluoro-alkyl group, and a process for their preparation, consisting in reacting the corresponding perfluoroimine with $H_2O_2$, in the presence of a base in a dipolar aprotic solvent.

2 Claims, No Drawings

PERFLUORO-AMINO-OXAZIRIDINES

DESCRIPTION OF THE INVENTION

The present invention relates to a new type of perfluoro-oxaziridine and to a process for their preparation.

The perfluoro-oxaziridines of the present invention are characterized by the presence of an aminic group in the position 3 of the oxaziridine ring, according to the following formula:

$$R_3C-N\overset{O}{\underset{}{\triangle}}CF-N\begin{matrix}CR_3\\CR_3\end{matrix}$$

wherein each R is independently either F or a perfluoro-alkyl radical having from 1 to 10 carbon atoms.

The perfluoro-oxaziridines are a little known class of organic compounds. The simplest, having the formula:

$$F_3C-N\overset{O}{\underset{}{\triangle}}CF_2,$$

has been described by Falardeau and DesMarteau in the "Journal of the American Chemical Society," 98, page 3529 (1976). The process for the preparation of this compound comprises the synthesis of a potentially explosive hydroperoxide difficult to prepare. The process, however, turns out to be absolutely ineffective for the preparation of oxaziridines substituted with perfluoroalkyl groups.

U.S. Pat. No. 4,287,128 describes oxaziridines of the formula:

$$R_2C\overset{O}{\underset{}{\triangle}}N-CR_3$$

wherein each R may independently be either fluorine or a perhalogenated alkyl radical having up to 10 carbon atoms with the exclusion of:

$$F_2C\overset{O}{\underset{}{\triangle}}N-CF_3$$

The process for the preparation of the perfluoroalkyl-oxaziridines consists or consists essentially in reacting a perfluoroalkylimine, as a starting compound, with gaseous chlorine in the presence of a carbonate or bicarbonate of an alkali or alkaline earth metal, according to the reaction:

$$M_2CO_3 + Cl_2 + CR_3-N=CR_2 \longrightarrow$$

$$R_3CN\overset{O}{\underset{}{\triangle}}CR_2 + CO_2 + 2\ MCl.$$

The reaction temperature for such a process is between $-20°$ C. and $+100°$ C.

According to said process, it is indispensable that in the reaction mixture there be present traces of water in order to catalyze the described reaction.

It is important to note that the water must be sufficient for forming the hypochlorite with the reacting chlorine, though it is not specified how much water it is possible to add; in fact, it must be noted that the oxaziridines described in U.S. patent No. 4,287,128 may, with the $H_2O$, easily undergo hydrolysis.

These compounds are in fact particularly reactive and may very easily be hydrolyzed to aldehydes and $\beta$-alkylhydroxylamines, as suggested in the cited U.S. patent itself.

For instance, it is not possible to prepare the first compound of the series, starting from $CF_3-N=CF_2$, by the above described method. For the preparation of said first compound of the series the cited complex DesMarteau method proves quite effective, although it shows the previously mentioned drawbacks.

The process described in U.S. patent No. 4,287,128, moreover, shows other disadvantages, such as for instance the need for regulation (adjustment) of the percentage of water that acts as a catalyst and of the proper quantity of gaseous chlorine to be introduced into the reaction mixture depending on the active surface of the catalyst. In fact, in the presence of gaseous chlorine the catalyst tends to easily become inactive during the course of the reaction.

In U.S. Pat. No. 3,358,003 there is described a process that is similar for the preparation of epoxides from the corresponding perfluoroinated olefins in the presence of bases and hydrogen peroxide.

Surprisingly, in accordance with the present invention it has been discovered that, notwithstanding the tendency of the oxaziridines to hydrolyze, it is possible to prepare said compounds by reacting perfluoroalkylimines with a base, preferably a carbonate or bicarbonate of an alkali or alkaline earth metal, in the presence of $H_2O_2$ and, possibly, of a solvent such as acetonitrile or diglyme, thus overcoming all the drawbacks of U.S. Pat. No. 4,287,128.

Moreover, as far as U.S. Pat. No. 3,358,003 is concerned, it is important to note the marked difference between the epoxidic group in comparison with oxaziridine as well as the by no means negligible fact that for the preparation of the epoxides there are especially recommended as solvents aliphatic alcohols, acetone or acetaldehyde which, on the contrary, do not favor the conversion of oxaziridines, for the preparation of which the use of solvents such as acetonitrile or diglyme is particularly recommended.

Thus, a further object of the present invention is that of providing a process for the preparation of perfluorooxaziridines of the formula:

$$R_3C-N\overset{O}{\underset{}{\triangle}}C\begin{matrix}R\\R_n\end{matrix}$$

wherein each R is, independently, either F or a perfluoroalkyl group having from 1 to 10 carbon atoms, while $R_n$ may be either a perfluoroalkyl group having from 1 to 10 carbon atoms or an amino group of the type:

$$-N\begin{matrix}CR_3\\CR_3\end{matrix}$$

wherein R has the meaning indicated previously, said process consisting in reacting a perfluoroimine of the type:

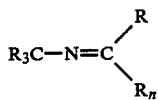

wherein R and $R_n$ have the meanings indicated above, with $H_2O_2$ in the presense of a base in a dipolar aprotic solvent, at a temperature between $-50°$ and $+50°$ C.

Preferably use is made of carbonates or bicarbonates of alkali metals or of alkaline earth metals as bases, and of diglyme or acetonitrile as dipolar aprotic solvents.

The contact times are not limitative in the present invention, though it is preferable to conduct the reaction in a time between 1 minute and 60 minutes, depending on the chosen reaction temperature.

With the process of the present invention it is possible to prepare any perfluoro-oxaziridine having as terminal groups F and perfluoroalkyl radicals except:

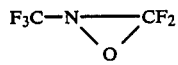

Amongst the oxaziridines prepared by means of the process of the present invention are preferred the perfluoroamino-oxaziridines of the formula:

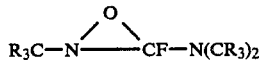

wherein each R may be either fluorine or a perfluoroalkyl group having up to 10 carbon atoms.

Particularly preferred is 2-(trifluoromethyl)-3-fluoro-3-bis(trifluoromethyl)aminooxaziridine of the formula:

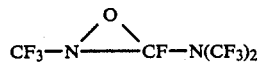

The oxaziridines of the present invention are useful as intermediates in the preparation of nitrons. Moreover, they form complexes with ions of transition metals and can be used as catalysts in the photochemical polymerization of ethylenic monomers.

Furthermore they may polymerize and copolymerize, forming liquids with a high thermal stability.

The Examples given below are intended merely for illustrative purposes and are in no way limitative of the present invention.

EXAMPLE 1

Into a 0.5 liter glass flask fitted with a magnetic stirrer, there were loaded 9 g of sodium bicarbonate, 100 ml of acetonitrile, 6.3 ml of hydrogen peroxide at 50% concentration and, through standard distillation techniques, 7.9 g of 1-bis(trifluoromethyl)aminotetrafluoro-2-aza-1-propylene.

The thus-loaded reactor was maintained at a temperature of 0° C. for 1 hour, under stirring. The raw reaction product was thereupon distilled at a pressure of $10^{-3}$ torr.

The vapors coming from the distillation boiler were then made to pass through refrigerated (cooled) traps kept at temperatures respectively of $-75°$ C. and of $-120°$ C.

In the trap at $-75°$ C. there condensed acetonitrile and the water, while, in the trap kept at $-120°$ C. there condensed 4.2 g of the desired product, 2-(trifluoromethyl)-3-fluoro-3-bis(trifluoromethyl)amino oxaziridine, in substantially the pure state. The $CO_2$ by-product, on the contrary, was removed by the dynamic vacuum during the distillation itself.

The conversion of the starting product was complete. The yield, defined as the ratio between the moles of desired product and the moles of reacted starting product, amounted to 50%.

| Physical properties and characterization of the product: | |
|---|---|
| Boiling point | 41° C. |
| Melting point | $-130°$ C. |

Infrared spectrum main absorption bands:

$cm^{-1}$ (intensity), 1422 (f), 1358 (m.f.), 1307 (m.f.), 1224 (m.f.), 1198 (m.f.), 1052 (d) (m.f. = very strong; f = strong; m = medium; d = weak).

NMR spectrum $^{19}F$: (internal reference $CFCl_3$, solvent $CDCl_3$).

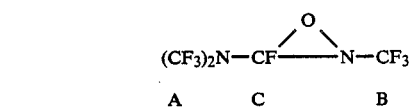

$\delta FA = (d) -56.6$ PPM JAC $= 6.1$ Hz
$\delta FB = (d) -65.7$ PPM JBC $= 18.3$ Hz
$\delta FC = (m) -100$ PPM

EXAMPLE 2

Following the same operational procedures described in Example 1, this time instead of sodium bicarbonate sodium carbonate was used.

Into a 0.5 liter glass flask fitted with a magnetic stirrer, there were loaded: 9 g of sodium carbonate; 100 ml acetonitrile; 6.3 ml of hydrogen peroxide and, through standard distillation techniques, 7.9 g of 1-bis(trifluoromethyl)aminotetrafluoro-2-aza-1-propylene.

The thus-loaded reactor was maintained under stirring for 1 hour, at 0° C.

The reaction product was then distilled at a pressure of $10^{-3}$ torr in the same way as in Example 1. In the $-120°$ C. trap 4.6 g of substantially pure 2-(trifluoromethyl)-3-fluoro-3-bis(trifluoromethyl)amino-oxaziridine were collected.

The conversion of the starting product was complete, and the yield, defined as in Example 1, amounted to 55%.

EXAMPLE 3

Into a 0.25 liter glass flask fitted with a magnetic stirrer, there were loaded: 4.5 g of sodium bicarbonate, 50 ml diglyme, 3 ml of hydrogen peroxide at 50% concentration, and through standard distillation techniques, 3.8 g of 1-bis(trifluoromethyl)aminotetrafluoro-2-aza-1-propylene.

The so-loaded reactor was maintained under constant stirring for 15 minutes at 0° C.

The raw reaction product then distilled at a pressure of $10^{-3}$ torr, in the same way as in Example 1.

In the trap at −75° C. there were collected diglyme and water, while in the trap at −120° C. there were collected 0.65 g of 2-(trifluoromethyl)-3-fluoro-3-bis(trifluoromethyl)amino-oxaziridine, in the substantially pure state.

The conversion of the starting material was complete, and the yield, defined as in Example 1, amounted to 16%.

EXAMPLE 4 (COMPARATIVE EXAMPLE)

Following the identical operational procedures as those used in Example 3, but in the absence of a basic catalyst, into a 250 ml glass flask fitted with a magnetic stirrer, there were loaded 50 ml of diglyme, 3 ml of hydrogen peroxide at 50% concentration and, through standard distillation techniques, 3.8 g of 1-bis(trifluoromethyl)amino-tethrafluoro-2-aza-1-propylene.

The thus-loaded reactor was kept under constant stirring for 15 minutes at 0° C.

The raw reaction product was distilled at a pressure of $10^{-3}$ torr, in the same way as that of Example 3. In the trap at −120° C. substantially pure 0.22 g of 2-(trifluoromethyl)-3-fluoro-3-bis(trifluoromethyl)-amino-oxaziridine was collected.

The conversion of the starting reaction product amounted to 60% while the yield equaled 5%.

EXAMPLE 5

Into a 100 milliliter glass flask fitted with a magnetic stirrer, there were loaded 2 g of sodium bicarbonate, 20 ml of acetonitrile, 1 ml of $H_2O_2$ at 50% b.w., and 5 g of perfluoro (6-aza-d-undecene):

$$CF_3-(CF_2)_4-N=CF-(CF_2)_3-CF_3$$

The thus-loaded reactor was maintained at a temperature of 0° C. for 1 hour under constant stirring.

The raw reaction product was thereupon distilled at a pressure of $10^{-3}$ torr.

The vapors coming from the distillation boiler were then passed through refrigerated traps kept at temperatures respectively of −40° C. and 120° C.

In the −120° C. trap, acetonitrile and some water were condensed, while in the trap kept at −40° C. there condensed 2 g of 2-(perfluoropentyl)-3-(perfluorobutyloxaziridine):

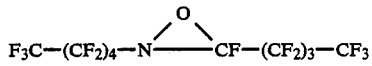

The oxaziridine contained some ppm of water. It was easily distilled over $Na_2SO_4$. The $CO_2$ was removed during the distillation step. The conversion of the starting product was complete.

The yield, defined as in Example 1, amounted to 38%.

What is claimed is:

1. Perfluoro-oxaziridines characterized by the presence of an aminic group in position 3 of the oxaziridine ring, of the formula:

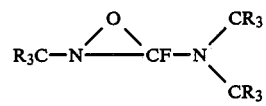

where each R is independently either F or a perfluoroalkyl group having from 1 to 10 carbon atoms.

2. Perfluoro-oxaziridine of claim 1, characterized in that each R is F.

* * * * *